US008718995B2

(12) United States Patent
Sarkisians (10) Patent No.: US 8,718,995 B2
(45) Date of Patent: May 6, 2014

(54) SYSTEM AND METHOD FOR DETERMINING COMPATIBILITY OF BIOACTIVE AGENTS AND FORMULATIONS PROVIDED THEREFROM

(76) Inventor: Natalia Sarkisians, Oakland, CA (US)

( * ) Notice: Subject to any disclaimer, the term of this patent is extended or adjusted under 35 U.S.C. 154(b) by 0 days.

(21) Appl. No.: 13/373,567

(22) Filed: Nov. 18, 2011

(65) Prior Publication Data

US 2013/0129716 A1      May 23, 2013

(51) Int. Cl.
  *G06G 7/58*   (2006.01)
  *G01N 33/48*  (2006.01)
(52) U.S. Cl.
  USPC .............................................. 703/11; 702/19
(58) Field of Classification Search
  CPC .............................. G06F 19/707; A61K 8/671
  See application file for complete search history.

(56) References Cited

U.S. PATENT DOCUMENTS

| | | | | |
|---|---|---|---|---|
| 2002/0177167 | A1* | 11/2002 | Levinson et al. | 435/7.1 |
| 2003/0059837 | A1* | 3/2003 | Levinson et al. | 435/7.1 |
| 2005/0089923 | A9* | 4/2005 | Levinson et al. | 435/7.1 |
| 2005/0118637 | A9* | 6/2005 | Levinson et al. | 435/7.1 |

* cited by examiner

*Primary Examiner* — Eric S DeJong
(74) *Attorney, Agent, or Firm* — Risto A. Rinne, Jr.

(57) ABSTRACT

A method for determining compatibility of bioactive agents (i.e. supplement formulation components, pharmacological agents, etc.), comprising (i) determining compatibility by and between components contained in a supplement formulation, i.e. vitamins and/or minerals, (ii) determining compatibility by and between the formulation components and the body, and (iii) determining compatibility by and between the formulation components and pharmacological agents, i.e. prescribed and over-the-counter medications, and formulations derived therefrom.

11 Claims, 8 Drawing Sheets

Dietary Reference Intakes (DRIs): Recommended Dietary Allowances and Adequate Intakes, Vitamins Food and Nutrition Board, Institute of Medicine, National Academies

| Life Stage Group | Vitamin A (µg/d)a | Vitamin C (mg/d) | Vitamin D (µg/d)b,c | Vitamin E (mg/d)d | Vitamin K (µg/d) | Thiamin (mg/d) | Riboflavin (mg/d) | Niacin (mg/d)e | Vitamin B6 (mg/d) | Folate (µg/d)f | Vitamin B12 (µg/d) | Pantothenic Acid (mg/d) | Biotin (µg/d) | Choline (mg/d)g |
|---|---|---|---|---|---|---|---|---|---|---|---|---|---|---|
| Infants | | | | | | | | | | | | | | |
| 0 to 6 mo | 400* | 40* | 10 | 4* | 2.0* | 0.2* | 0.3* | 2* | 0.1* | 65* | 0.4* | 1.7* | 5* | 125* |
| 6 to 12 mo | 500* | 50* | 10 | 5* | 2.5* | 0.3* | 0.4* | 4* | 0.3* | 80* | 0.5* | 1.8* | 6* | 150* |
| Children | | | | | | | | | | | | | | |
| 1–3 y | 300 | 15 | 15 | 6 | 30* | 0.5 | 0.5 | 6 | 0.5 | 150 | 0.9 | 2* | 8* | 200* |
| 4–8 y | 400 | 25 | 15 | 7 | 55* | 0.6 | 0.6 | 8 | 0.6 | 200 | 1.2 | 3* | 12* | 250* |
| Males | | | | | | | | | | | | | | |
| 9–13 y | 600 | 45 | 15 | 11 | 60* | 0.9 | 0.9 | 12 | 1.0 | 300 | 1.8 | 4* | 20* | 375* |
| 14–18 y | 900 | 75 | 15 | 15 | 75* | 1.2 | 1.3 | 16 | 1.3 | 400 | 2.4 | 5* | 25* | 550* |
| 19–30 y | 900 | 90 | 15 | 15 | 120* | 1.2 | 1.3 | 16 | 1.3 | 400 | 2.4 | 5* | 30* | 550* |
| 31–50 y | 900 | 90 | 15 | 15 | 120* | 1.2 | 1.3 | 16 | 1.3 | 400 | 2.4 | 5* | 30* | 550* |
| 51–70 y | 900 | 90 | 15 | 15 | 120* | 1.2 | 1.3 | 16 | 1.7 | 400 | 2.4h | 5* | 30* | 550* |
| >70 y | 900 | 90 | 20 | 15 | 120* | 1.2 | 1.3 | 16 | 1.7 | 400 | 2.4h | 5* | 30* | 550* |
| Females | | | | | | | | | | | | | | |
| 9–13 y | 600 | 45 | 15 | 11 | 60* | 0.9 | 0.9 | 12 | 1.0 | 300 | 1.8 | 4* | 20* | 375* |
| 14–18 y | 700 | 65 | 15 | 15 | 75* | 1.0 | 1.0 | 14 | 1.2 | 400i | 2.4 | 5* | 25* | 400* |
| 19–30 y | 700 | 75 | 15 | 15 | 90* | 1.1 | 1.1 | 14 | 1.3 | 400i | 2.4 | 5* | 30* | 425* |
| 31–50 y | 700 | 75 | 15 | 15 | 90* | 1.1 | 1.1 | 14 | 1.3 | 400i | 2.4 | 5* | 30* | 425* |
| 51–70 y | 700 | 75 | 15 | 15 | 90* | 1.1 | 1.1 | 14 | 1.5 | 400 | 2.4h | 5* | 30* | 425* |
| >70 y | 700 | 75 | 20 | 15 | 90* | 1.1 | 1.1 | 14 | 1.5 | 400 | 2.4h | 5* | 30* | 425* |
| Pregnancy | | | | | | | | | | | | | | |
| 14–18 y | 750 | 80 | 15 | 15 | 75* | 1.4 | 1.4 | 18 | 1.9 | 600i | 2.6 | 6* | 30* | 450* |
| 19–30 y | 770 | 85 | 15 | 15 | 90* | 1.4 | 1.4 | 18 | 1.9 | 600i | 2.6 | 6* | 30* | 450* |
| 31–50 y | 770 | 85 | 15 | 15 | 90* | 1.4 | 1.4 | 18 | 1.9 | 600i | 2.6 | 6* | 30* | 450* |
| Lactation | | | | | | | | | | | | | | |
| 14–18 y | 1,200 | 115 | 15 | 19 | 75* | 1.4 | 1.6 | 17 | 2.0 | 500 | 2.8 | 7* | 35* | 550* |
| 19–30 y | 1,300 | 120 | 15 | 19 | 90* | 1.4 | 1.6 | 17 | 2.0 | 500 | 2.8 | 7* | 35* | 550* |
| 31–50 y | 1,300 | 120 | 15 | 19 | 90* | 1.4 | 1.6 | 17 | 2.0 | 500 | 2.8 | 7* | 35* | 550* |

FIG. 1A

Dietary Reference Intakes (DRIs): Recommended Dietary Allownaces and Adequate Intakes, Elements
Food and Nutrition Board, Institute of Medicine, National Academies

| Life Stage Group | Calcium (mg/d) | Chromium (μg/d) | Copper (μg/d) | Flouride (mg/d) | Iodine (μg/d) | Iron (mg/d) | Magnesium (mg/d) | Manganese (mg/d) | Molybdenum (μg/d) | Phosphorus (mg/d) | Selenium (μg/d) | Zinc (mg/d) | Potassium (g/d) | Sodium (g/d) | Chloride (g/d) |
|---|---|---|---|---|---|---|---|---|---|---|---|---|---|---|---|
| Infants | | | | | | | | | | | | | | | |
| 0 to 6 mo | 200* | 0.2* | 200* | 0.01* | 110* | 0.27* | 30* | 0.003* | 2* | 100* | 15* | 2* | 0.4* | 0.12* | 0.18* |
| 6 to 12 | 260* | 5.5* | 220* | 0.5* | 130* | 11 | 75* | 0.6* | 3* | 275* | 20* | 3 | 0.7* | 0.37* | 0.57* |
| Children | | | | | | | | | | | | | | | |
| 1–3 y | 700 | 11* | 340 | 0.7* | 90 | 7 | 80 | 1.2* | 17 | 460 | 20 | 3 | 3.0* | 1.0* | 1.5* |
| 4–8 y | 1,000 | 15* | 440 | 1* | 90 | 10 | 130 | 1.5* | 22 | 500 | 30 | 5 | 3.8* | 1.2* | 1.9* |
| Males | | | | | | | | | | | | | | | |
| 9–13 y | 1,300 | 25* | 700 | 2* | 120 | 8 | 240 | 1.9* | 34 | 1,250 | 40 | 8 | 4.5* | 1.5* | 2.3* |
| 14–18 y | 1,300 | 35* | 890 | 3* | 150 | 11 | 410 | 2.2* | 43 | 1,250 | 55 | 11 | 4.7* | 1.5* | 2.3* |
| 19–30 y | 1,000 | 35* | 900 | 4* | 150 | 8 | 400 | 2.3* | 45 | 700 | 55 | 11 | 4.7* | 1.5* | 2.3* |
| 31–50 y | 1,000 | 35* | 900 | 4* | 150 | 8 | 420 | 2.3* | 45 | 700 | 55 | 11 | 4.7* | 1.5* | 2.3* |
| 51–70 y | 1,000 | 30* | 900 | 4* | 150 | 8 | 420 | 2.3* | 45 | 700 | 55 | 11 | 4.7* | 1.3* | 2.0* |
| >70 y | 1,200 | 30* | 900 | 4* | 150 | 8 | 420 | 2.3* | 45 | 700 | 55 | 11 | 4.7* | 1.2* | 1.8* |
| Females | | | | | | | | | | | | | | | |
| 9–13 y | 1,300 | 21* | 700 | 2* | 120 | 8 | 240 | 1.6* | 34 | 1,250 | 40 | 8 | 4.5* | 1.5* | 2.3* |
| 14–18 y | 1,300 | 24* | 890 | 3* | 150 | 15 | 360 | 1.6* | 43 | 1,250 | 55 | 9 | 4.7* | 1.5* | 2.3* |
| 19–30 y | 1,000 | 25* | 900 | 3* | 150 | 18 | 310 | 1.8* | 45 | 700 | 55 | 8 | 4.7* | 1.5* | 2.3* |
| 31–50 y | 1,000 | 25* | 900 | 3* | 150 | 18 | 320 | 1.8* | 45 | 700 | 55 | 8 | 4.7* | 1.5* | 2.3* |
| 51–70 y | 1,200 | 20* | 900 | 3* | 150 | 8 | 320 | 1.8* | 45 | 700 | 55 | 8 | 4.7* | 1.3* | 2.0* |
| >70 y | 1,200 | 20* | 900 | 3* | 150 | 8 | 320 | 1.8* | 45 | 700 | 55 | 8 | 4.7* | 1.2* | 1.8* |
| Pregnanc | | | | | | | | | | | | | | | |
| 14–18 y | 1,300 | 29* | 1,000 | 3* | 220 | 27 | 400 | 2.0* | 50 | 1,250 | 60 | 12 | 4.7* | 1.5* | 2.3* |
| 19–30 y | 1,000 | 30* | 1,000 | 3* | 220 | 27 | 350 | 2.0* | 50 | 700 | 60 | 11 | 4.7* | 1.5* | 2.3* |
| 31–50 y | 1,000 | 30* | 1,000 | 3* | 220 | 27 | 360 | 2.0* | 50 | 700 | 60 | 11 | 4.7* | 1.5* | 2.3* |
| Lactation | | | | | | | | | | | | | | | |
| 14–18 y | 1,300 | 44* | 1,300 | 3* | 290 | 10 | 360 | 2.6* | 50 | 1,250 | 70 | 13 | 5.1* | 1.5* | 2.3* |
| 19–30 y | 1,000 | 45* | 1,300 | 3* | 290 | 9 | 310 | 2.6* | 50 | 700 | 70 | 12 | 5.1* | 1.5* | 2.3* |
| 31–50 y | 1,000 | 45* | 1,300 | 3* | 290 | 9 | 320 | 2.6* | 50 | 700 | 70 | 12 | 5.1* | 1.5* | 2.3* |

| Micronutrient | Interactions with other vitamins or minerals | | Characteristics of interactions |
|---|---|---|---|
| Iron | Calcium, Zinc | − | Both reduce the absorption of Iron. |
| | Vitamin A | + | Increases the absorption of iron. Their combined intake reverberates in higher hemoglobin levels in comparison to Iron standalone intake. |
| | Vitamin C | + | Increases the absorption of Iron in the gastrointestinal tract. |
| Calcium | Vitamin D | + | Increases bioavailability of Calcium, enhances Calcium absorption by bone tissue. |
| | Magnesium | − | Reduces the absorption of Calcium. |
| | Zinc | − | Reduces the absorption of Calcium. |
| Magnesium | Vitamin B6 | + | Promotes the absorption and retention of Magnesium in cells. |
| | Calcium | − | Reduces the absorption of Magnesium. |
| Manganese | Calcium, Iron | − | Both diminish the absorption of Manganese. |
| Copper | Zinc | − | Reduces the absorption of Copper. |
| Molybdenum | Copper | − | Reduces the absorption of Molybdenum. |
| Zinc | Vitamin B9 (Folic acid) | − | Prevents the absorption of Zinc by forming insoluble complexes. |
| | Calcium, Iron, Copper | − | All reduce the absorption of Zinc. |
| | Vitamin B2 | + | Increases the bioavailability of Zinc. |
| Chrome | Iron | − | Reduces the absorption of Chromium. |
| Vitamin A | Vitamin C, Vitamin E | + | Both protect vitamin A from the oxidation |
| | Zinc | + | Participates in the transformation of Vitamin A in its active form. |
| Vitamin B1 | Vitamin B6 | − | Inhibits the transformation of Vitamin B1 in its bio-active form. |
| | Vitamin B12 | − | Enhances allergic reaction to vitamin B1 and destroys its structure. |
| Vitamin B6 | Vitamin B12 | − | Destroys Vitamin B6. |
| Vitamin B9 | Zinc | − | Prevents the absorption of vitamin B9 by forming insoluble complexes. |
| | Vitamin C | + | Helps to conserve Vitamin B9 in body tissues. |
| Vitamin B12 | Vitamin C, Vitamin B1, Iron, Copper | − | Turns vitamin B12 into a useless substance. |
| Vitamin E | Vitamin C | + | Restores oxidized vitamin E. |
| | Selenium | + | Have a bilateral antioxidant effect. |

*FIG. 3*

LUCID SOLO MOOD CONTROL

|  |  | % DV |
|---|---|---|
| Vitamin B6 | 2 MG | 100 |
| Magnesium | 300 mg | 75 |
| GABA | 500 mg | * |
| Tulsi (leaf) | 100 mg | * |
| L-theanine | 100 mg | * |
| Schissandra Fruit extract | 90 mg | * |
| Rhodiola rosea Root extract | 50 mg | * |
| Ashwagandha root extract | 50 mg | * |
| Avena sativa (leaf and stem) (oat straw) | 50 mg | * |
| American ginseng | 50 mg | * |
| Eleutherococcus senticosus (root) | 20 mg | * |

*FIG. 4A*

LUCID TRIO Age-control 50+

Iron plus

| | | %DV |
|---|---|---|
| Vitamin A | 2500 IU | 50% |
| Vitamin C | 60 mg | 100% |
| Thiamine | 1.5 mg | 100% |
| Folic acid | 400 mcg | 100% |
| Iron | 13 mg | 72% |
| Copper | 2 mg | 100% |

Antioxidants plus

| | | %DV |
|---|---|---|
| Vitamin A | 2500 IU | 50% |
| Vitamin E | 30 IU | 100% |
| Riboflavin | 1.7 mg | 100% |
| Niacin | 16 mg | 80% |
| Vitamin B6 | 2 mg | 100% |
| Iodine | 150 mcg | 100% |
| Magnesium | 60 mg | 15% |
| Zinc | 15 mg | 100% |
| Selenium | 56 mcg | 80% |
| Manganese | 2 mg | 100% |
| Lycopene | 5 mg | * |
| Lutein | 5 mg | * |

Calcium D3 plus

| | | %DV |
|---|---|---|
| Vitamin D3 | 400 IU | 100% |
| Vitamin K1 | 44 mcg | 55% |
| Vitamin B12 | 6 mcg | 100% |
| Pantothenic acid | 10 mg | 100% |
| Biotin | 180 mcg | 60% |
| Calcium | 300 mg | 30% |
| Chromium | 48 mcg | 40% |

*FIG. 4B*

LUCID TRIO VITAMIN & MINERAL COMPLEX

| TABLET 1 | IRON PLUS | %DV |
|---|---|---|
| Vitamin A | 2500 IU | 50% |
| Vitamin C | 30 mg | 50% |
| Thiamine | 1,5 mg | 100% |
| Folic acid | 200 mcg | 50% |
| Iron | 18 mg | 100% |
| Copper | 2 mg | 100% |

| TABLET 2 | Antioxidants plus | %DV |
|---|---|---|
| Vitamin A | 2500 IU | 50% |
| Vitamin C | 30 mg | 50% |
| Vitamin E | 30 IU | 100% |
| Riboflavin | 1.7 mg | 100% |
| Niacin | 20 mg | 100% |
| Vitamin B6 | 2 mg | 100% |
| Iodine | 150 mcg | 100% |
| Magnesium | 50 mg | 13% |
| Zinc | 15 mg | 100% |
| Selenium | 70 mcg | 100% |
| Manganese | 2 mg | 100% |
| Molibdenum | 75 mcg | 100% |

| TABLET 3 | Calcium-D3 | %DV |
|---|---|---|
| Vitamin D3 | 400IU | 100% |
| Vitamin K1 | 80 mcg | 100% |
| Folic acid | 200 mcg | 50% |
| Vitamin B12 | 6 mcg | 100% |
| Biotin | 300 mcg | 100% |
| Pantothenic acid | 10 mg | 100% |
| Calcium | 100 mg | 10% |
| Chromium | 120 mcg | 100% |

*FIG. 4C*

LUCID TRIO Diet

| Calcium D3+ | | % DV | Antioxidants+ | | % DV | Iron + | | % DV |
|---|---|---|---|---|---|---|---|---|
| Vitamin D3 | 400 IU | 100 | Vitamin A | 1500 IU | 30 | A | 2500 IU | 50 |
| Vitamin K1 | 80 mcg | 100 | Vitamin C | 30 mg | 50 | Vitamin C | 30 mg | 50 |
| Folic acid | 200 mcg | 50 | Vitamin E | 30 IU | 100 | Thiamine | 1.5 mg | 100 |
| Vitamin B12 | 6 mcg | 100 | Ribofalvin | 1.7 mg | 100 | Folic acid | 200 mcg | 50 |
| Biotin | 300 mcg | 100 | Niacin | 20 mg | 100 | Iron | 18 mg | 100 |
| Pantothenic acid | 10 mg | 100 | Vitamin B6 | 2 mg | 100 | Copper | 2 mg | 100 |
| Calcium | 120 mg | 12 | Iodine | 150 mcg | 100 | Inulin | 200 mg | * |
| Succinic acid | 30 mg | * | Magnesium | 40 mg | 10 | Melissa leaf extract | 30 mg | * |
| L-carnitine | 60 mg | * | Zinc | 15 mg | 100 | | | |
| Green tea leaf extract | 30 mg | * | Selenium | 70 mcg | 100 | | | |
| Caffeine anhydrous | 10 mg | * | Manganese | 2 mg | 100 | | | |
| | | | Chromium | 120 mcg | 100 | | | |
| | | | Lipoic acid | 15 mg | * | | | |
| | | | Inulin | 200 mg | * | | | |

*FIG. 4D*

SYSTEM AND METHOD FOR DETERMINING COMPATIBILITY OF BIOACTIVE AGENTS AND FORMULATIONS PROVIDED THEREFROM

FIELD OF THE PRESENT INVENTION

The present invention relates generally to vitamin and mineral formulations. More particularly, the invention relates to a system and method for determining the compatibility between individual bioactive agents, and bioactive agents and the body, and formulations derived therefrom.

BACKGROUND OF THE INVENTION

As is well known in the art, vitamins and minerals are required for the regulation of the body's metabolic functions, and are found naturally in the foods that we eat. Many foods are thus fortified in order to provide additional nutrients, or to replace nutrients that may have been lost during the processing of the food, and/or harvesting and/or storage.

Many people are able to obtain satisfactory nutrition from the wide selection of foods available in the United States. However, if a person's diet is nutritionally deficient or a special health condition exists, then a vitamin and mineral supplement from a secondary source is necessary.

Although people can, and in many instances do, obtain satisfactory nutrition from available food sources, many people ingest vitamin and/or mineral supplements as a "safety measure". Unfortunately, the dosage of the vitamins and minerals ingested is often in excess of the body's requirements. As discussed below, large doses of vitamin and mineral supplements can, and in many instances will, adversely affect body function.

As is also well known in the art, there are several individual vitamins, which are required by the human body to maintain normal body function. These vitamins include vitamins A, C, D, E, K, Choline, and the members of the B vitamin group: vitamins B1 (thiamin), B2 (riboflavin), B6, B12, niacin and folate, biotin and pantothenic acid.

Vitamins are typically classified on the basis of their ability to dissolve in fat or in water. The fat-soluble vitamins, i.e. vitamins A, D, E, and K, are generally found in the fats of foods, nuts, vegetables and fruits.

In the event of excessive consumption of fat soluble vitamins, the excess will be stored in body fat tissues. This can lead to unwanted toxic buildup of certain vitamins; particularly, vitamins A, and D, and can cause teratogenic effects in the future (i.e. inherent birth defects in children).

Each of the fat-soluble vitamins performs a unique function in the body. Vitamin A is a very important fat-soluble vitamin. The functions of vitamin A include:

Vitamin A regulates the process of protein synthesis, promotes normal metabolism, plays an important role in the formation of bones and teeth, is responsible for the growth of new cells, and slows down the aging process.

Vitamin A is long-known for vital effects on eye sight. It ensures the normal activity of the visual analyzer and participates in the synthesis of visual pigment of the retina and the perception of the light beam by the eye.

Vitamin A is necessary for normal functioning of the immune system and is an integral part of the process of combating infections. Retinol is essential for the maintenance and restoration of epithelial tissues; which are made of skin and mucous integument.

Vitamin A has beneficial effects on lung function due to its close link with the mucous membrane and epithelial cells. Vitamin A is involved in the synthesis of the steroid hormones (including progesterone).

Both Retinoids, a Vitamin A group, and Carotenoids are powerful antioxidants. They serve to protect cell membranes of the brain from the destructive effect of free radicals.

Vitamin D is another fat-soluble vitamin, which plays a role in the differentiation of cells in the intestines, skin, immune system, and bones. Vitamin D also regulates blood calcium levels, which are important in maintaining proper bone density.

A toxic or excess amount of vitamin D can similarly cause adverse organ function. The main consequence of vitamin D toxicity is a buildup of calcium in your blood (hypercalcemia), which can cause hard lumps of calcium in muscles and organs, heart rhythm abnormalities, kidney stones. Polyuria (i.e. frequent urination), muscle weakness, and nausea and gastro discomfort.

Although vitamin D toxicity is rare (even among people who take supplements), it has been found that the risk of vitamin D toxicity (and the adverse consequences resulting therefrom) is significantly greater for a person experiencing abnormal liver or kidney function or ingesting thiazide-type diuretics.

Vitamin E is another important fat-soluble vitamin, which is also considered and, hence, often referred to as an antioxidant. Vitamin E inserts itself into cell membranes and protects substances inside the cells, such as Deoxyribonucleic acid (DNA), from being chemically modified by oxygen-like molecules.

An excess amount of vitamin E can similarly cause adverse physiological consequences. Indeed, it is well known that excess amounts of vitamin E can, and in many instances will, increase the risk of bleeding (including bleeding within the brain, which can cause a stroke); particularly, for adults who are also ingesting an anticoagulant (especially Warfarin™). Adults who ingest excess amounts of vitamin E can also experience muscle weakness, fatigue, nausea, and diarrhea.

Vitamin K is involved in synthesizing proteins that help blood clot. Vitamin K is also necessary for producing a key protein that is important in bone formation. In addition to dietary sources, vitamin K can also be derived from bacteria that reside in the intestines.

A Mayo Clinic Report suggests that an adequate intake of vitamin K can cut the risk of non-Hodgkin's lymphoma by almost 50%.

The water-soluble vitamins include vitamin C and the B-complex family of vitamins. Water-soluble vitamins are not stored in the body and are generally excreted with urine when consumed in excess of the body's needs. However, as discussed below, prior to excretion, an excess amount of some water-soluble vitamins; particularly, vitamins B6 and B12, can cause a number of physiological complications.

Vitamin C's roles include assisting in the production and maintenance of collagen, a protein found in bones, skin, and teeth. Vitamin C is also known to prevent scurvy and plays a role in wound repair. It is essential for the development and maintenance of connective tissues, it protects your immune system and reduces the severity of allergic reactions.

The vitamin B family of vitamins, which include vitamins B1 (thiamine), B2 (riboflavin), B3 (niacin), vitamin B5 (pantothenic acid), B6 (pyridoxine), B7 (biotin), B9 (folic acid), B12 (cyanocobalamin), support many body functions.

Vitamin B1 aids in the conversion of carbohydrates into energy and maintains the mucus membranes in good condition. An excess amount of vitamin B1 can, however, cause skin rashes, hypersensitivity and high blood pressure.

Vitamin B2 aids in maintaining a strong immune system and regulates the growth of red blood cells; protects mucous membranes. Being a coenzyme, vitamin B2 is responsible for digestion of proteins and carbohydrates.

Vitamin B3 (niacin) is involved in enzyme reactions, aids in the metabolism of carbohydrates and prevents alopecia and certain gastrointestinal disorders. An excess of vitamin B3 can damage liver tissues, cause insomnia, heartburn, high blood sugar and vomiting.

There are numerous benefits of vitamin B6. Vitamin B6 aids in the formation of antibodies and strengthens the immune system. It's essential for getting energy and nutrients from food. Vitamin B6 is also responsible for the formation of vitamin B3 in the body.

Excess vitamin B6 can, however, adversely affect nerve function; particularly, nerves in the hands, feet and toes. Excess vitamin B6 can also cause high blood pressure, low blood sugar, formation of kidney stones, insomnia, cramps, headaches, fatigue and mood swings.

Vitamin B12 prevents pernicious anemia and supports the development and maturation of red blood cells. Vitamin B12 also helps in maintaining a healthy nervous system and aids in speeding up metabolism.

Excess vitamin B12 can, however, similarly adversely affect nerve function and, in some instances, cause panic attacks, heart palpitations or hyperthyroid.

As indicated above, various minerals are also required to maintain normal body function. The major minerals, which typically require more than 100 mg/day, include sodium, potassium, calcium, phosphorus, magnesium, sulfur, and chloride. The trace minerals, which require less than 100 mg/day, include iron, zinc, copper, selenium, iodine, chromium, manganese, fluoride, molybdenum, cobalt and others. Each of the noted minerals performs a unique function in the body.

The noted minerals cannot be made in the body and must be obtained from ingested food, water and supplements. However, as discussed below, an excess amount of one or more minerals can produce toxic effects.

Magnesium is an important mineral that helps the body to maintain muscles, nerves, and bones. It is also employed to maintain optimum heart rhythm, energy metabolism and protein synthesis.

A deficiency of magnesium can cause sensitiveness to noise, nervousness, irritability, mental depression, confusion, twitching, trembling, apprehension, insomnia, muscle weakness and cramps in the toes, feet, legs, or fingers.

Calcium is another important mineral that is essential for healthy and strong bones and teeth. Calcium also ensures the proper functioning of muscles and nerves, and aids in blood clotting.

A deficiency of calcium can thus adversely affect bone and teeth formation, while an excess of calcium can lead to adverse kidney function and stones.

Potassium serves as an electrolyte and is involved in the balance of fluid within the body. It is important in controlling the activity of the heart, muscles, nervous system and virtually every cell in the body. Potassium also regulates the water balance and acid-base balance in the blood and tissues.

A deficiency of potassium can cause abnormal muscle function, e.g. weak muscles. An excess of potassium can cause an irregular heartbeat.

Selenium is an essential mineral that functions largely in the form of proteins, i.e. seleno-proteins, which act as enzymes and help prevent damage to cells in the body by oxidants in the environment or those produced by normal metabolism.

A deficiency of selenium can cause "Keshan" disease; a fatal form of cardiomyopathy (heart muscle disease). While an excess of selenium can cause balding and brittle nails, intestinal distress, weakness and slowed mental functioning.

Zinc is another essential mineral. Zinc is involved in the manufacture of protein and in cell division, protects nerve and brain tissues.

A deficiency of zinc can cause short stature, anemia, increased pigmentation of skin, enlarged liver and spleen (hepatosplenomegaly), impaired gonadal function, impaired wound healing, and immune deficiency. An excess of zinc can cause gastrointestinal irritation (upset stomach) and cause copper deficiency.

Chromium works with insulin (a hormone, produced in the pancreas) in assisting cells to absorb glucose and release energy. Chromium picolinate, i.e. a form of chromium, is a mineral that plays a vital role in processing carbohydrates and fats.

A deficiency of chromium can cause anxiety, fatigue, glucose intolerance (particularly in people with diabetes), inadequate metabolism of amino acids, and an increased risk of arteriosclerosis. An excess amount of chromium can cause dermatitis, intestinal ulcers, and kidney and liver impairment.

Deficiencies of some of the aforementioned vitamins and minerals can thus adversely affect body function. It is thus important that a person provides his/her body with a sufficient intake of vitamins and minerals daily.

Various sources, such as Food and Nutrition Board, Institute of Medicine, National Academies, publish the recommended intake values for vitamins and minerals. Illustrative are the daily recommended vitamin intake charts shown in FIGS. 1A and 1B.

As indicated above, many people are able to obtain satisfactory nutrition and, hence, the daily recommended intake of essential vitamins and minerals from the wide selection of foods available in the United States. However, if a person's diet is nutritionally deficient, then a vitamin and mineral supplement from a secondary source is needed.

There are, however, several drawbacks and disadvantages associated with vitamin and/or mineral supplements from secondary sources. One major drawback is that few individuals are knowledgeable of their individual vitamin and mineral requirements and are often confused by the multitude of supplements available through secondary sources. As a result, very few individuals purchase and ingest the appropriate supplement. Moreover, many people consume more vitamins and or minerals that are needed.

A further major drawback is that most, if not all, vitamin supplements comprise unbalanced and/or excessive amounts of one or more vitamins. For example, as shown in Table 1 below, a vitamin supplement from one secondary source includes the following dosages of vitamins B1 and B2:

TABLE I

| Vitamin | Daily Dose | % daily volume |
| --- | --- | --- |
| B1 (Thiamin) | 50 mg | 3333% |
| B2 (Riboflavin) | 50 mg | 2941% |

The noted amounts of B vitamins can, and in most instances will, result in undesirable stress on organs to process and excrete the excess amounts of the B vitamins. Further, since B vitamins are interdependent, excess quantities of one B vitamin can adversely affect the bioactivity of other B vitamins and, in some instances, can produce a deficiency of other B vitamins or an allergic reaction.

Many supplements also contain various additional ingredients and minerals e.g., chromium, iron, manganese, selenium, potassium, etc. In many instances, the noted materials are similarly provided in unbalanced and/or excessive amounts that can be toxic.

As is well known in the art, many minerals, such as iron and chromium, can build up in the body and adversely affect organ function. For example, a toxic amount (e.g., ≥25 mg) or buildup of iron can cause liver and heart damage (atherosclerosis). As stated above, a toxic amount (e.g., ≥50 mg) or buildup of chromium can cause dermatitis, intestinal ulcers, and kidney and liver impairment.

A further major drawback associated with vitamin (and mineral) supplements from secondary sources is that the secondary sources do not account for (i) formulation compatibility, i.e. compatibility by and between supplement formulation components, e.g., individual vitamins, minerals, fillers, etc., (ii) physiological compatibility, i.e. compatibility by and between formulation components and the body, or (iii) medicinal compatibility, i.e. compatibility by and between formulation components and pharmacological agents, i.e. prescribed and over-the-counter medications.

As discussed in detail herein, compatibility issues by and between formulation components, formulation components and the body, and formulation components and pharmacological agents can, and in many instances will, adversely affect the bioavailability of one or more formulation components and/or pharmacological agents.

Compatibility issues by and between formulation components, formulation components and the body, and formulation components and pharmacological agents can, and in many instances will, also adversely affect body function.

Based on publicly available sources of information, zinc is known to decrease absorption of copper and competes for absorption with iron and calcium, and calcium and iron reduce the absorption of manganese, thus combining in one pill or capsule specified minerals impose the need for an increased daily dosage in order to meet the daily norms. It is a known fact that not all of the vitamins and minerals are compatible with each other during prolonged storage and during the period of absorption time inside the human body.

Further, patients with diseases of the heart and blood vessels are often prescribed blood-thinning pharmacological agents or medications, such as Coumadin™ and Warfarin™. Vitamin K can interfere with such drugs.

While very low levels of vitamin K in the body can result in poor clot formation and increased bleeding, very high doses of ingested or administered vitamin K may act to counteract large doses of anticoagulants, placing the patient at risk for clot formation. Similarly, high levels of vitamin C (ascorbic acid) may interfere with anticoagulant inhibition of the clotting pathway and lead to increased risk for clot formation.

Many types of pharmacological agents that are used in the treatment of high blood pressure can also interact with high levels of supplemented vitamins. For example, antihypertensive pharmacological agents, which help lower blood pressure by dilating blood vessels, can be affected by increased levels of vitamin B3 (niacin). In high doses (>75 mg), niacin may dilate blood vessels and heighten the medication effects, resulting in dangerously low blood pressure. Digitalis-based drugs, such as Digoxin™ and Diltiazem™, can also be affected by vitamin D via alteration in blood calcium level and can induce irregular heartbeats, i.e. arrhythmias.

Other pharmacological agents, which treat high blood pressure by decreasing the amount of fluid in the body, called diuretics, can also be affected by vitamins. Thiazide diuretics act on the kidney to remove fluid, but retain minerals, such as calcium. Excessive vitamin D ingestion while on diuretic therapy can result in increased calcium in the blood. As in other vitamin D-drug interactions, increased blood calcium can also cause abnormal heartbeats, i.e. arrhythmias.

It would thus be desirable to provide a system and method for determining compatibility by and between supplement formulation components, formulation components and the body, and formulation components and pharmacological agents.

It is therefore an object of the present invention to provide a system and method for determining compatibility by and between supplement formulation components, formulation components and the body, and formulation components and pharmacological agents.

It is another object of the invention to provide a system and method for determining compatibility by and between supplement formulation components, formulation components and the body, and formulation components and pharmacological agents that can be tailored to an individual's specific physiology.

It is another object of the invention to provide a system and method for determining compatibility by and between supplement formulation components, formulation components and the body, and formulation components and pharmacological agents that is adapted to wirelessly receive and transmit data and information from/to a skilled party, e.g., physician or nutritionist.

It is another object of the invention to provide bioactive formulations and supplements based on determined compatibility by and between supplement formulation components, formulation components and the body, and formulation components and pharmacological agents that can be tailored to an individual's specific physiology.

SUMMARY OF THE INVENTION

In accordance with the above objects and those that will be mentioned and will become apparent below, the method for determining compatibility of bioactive agents (i.e. supplement formulation components, pharmacological agents, etc.), in accordance with one embodiment of the invention, generally comprises the steps of (i) determining compatibility by and between components contained in a supplement formulation, i.e. vitamins and/or minerals, (ii) determining compatibility by and between the formulation components and the body, and (iii) determining compatibility by and between the formulation components and pharmacological agents, i.e. prescribed and over-the-counter medications.

In some embodiments of the invention, the method also includes the step of determining compatibility by and between the formulation components and at least one food.

In accordance with another embodiment of the invention, there is provided a system for determining compatibility of bioactive agents, comprising memory means adapted to store selective data and information, and programming means having a plurality of integral assessment modules, the assessment modules including a formulation compatibility module that is adapted to determine compatibility by and between components contained in a supplement formulation, a physiological compatibility module that is adapted to determine compatibility by and between the formulation components and the body, and a medicinal compatibility module that is adapted to determine compatibility by and between the formulation components and pharmacological agents, i.e. prescribed and over-the-counter medications.

In some embodiments of the invention, the system includes means for comparing selective bioactive agents.

In some embodiments of the invention, the system includes wireless communication means for receiving and transmitting data and information from/to a monitoring station.

In accordance with another embodiment of the invention, there are provided balanced bioactive formulations of vitamins and/or minerals tailored to an individual's specific physiology, the formulations being based on determined compatibility by and between supplement formulation components, formulation components and the body, and formulation components and pharmacological agents.

In some embodiments of the invention, a unique color coding system is employed to identify specific vitamin and mineral formulations.

As discussed in detail herein, the present invention provides numerous advantages compared to prior art methods for determining vitamin and mineral formulations. Among the advantages are the following:

- The provision of balanced bioactive vitamin and mineral formulations that improve the health of the population by providing compatible compositions of vitamins and minerals based on their intricate chemical structure and behavior.
- The provision of balanced bioactive vitamin and mineral formulations that substantially reduce the probability of excessive intake of vitamins and minerals, while meeting existing USA FDA government levels of daily norms.
- The provision of methods for determining compatibility of vitamin and mineral formulations that improve the absorption of various vitamins and minerals or other elements that are part of vitamin-mineral complexes or supplements by creating proper conditions for their synergistic interaction.
- The provision of methods for determining compatibility of vitamin and mineral formulations that increase storage life for products containing compatible ingredients.
- The provision of methods for determining compatibility of vitamin and mineral formulations that reduce manufacturing time by eliminating the need for special coatings, which are traditionally used in non compatible vitamin/mineral complexes, therefore, reducing the eco foot print during the production. Manufacturing time can be reduced.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIGS. 1A and 1B are charts showing recommended daily allowances of vitamins and minerals;

FIG. 3 is a chart of several known negative and positive interactions between various vitamins and minerals.

DETAILED DESCRIPTION OF THE INVENTION

Before describing the present invention in detail, it is to be understood that this invention is not limited to particularly exemplified materials, methods or structures as such may, of course, vary. Thus, although a number of systems and methods similar or equivalent to those described herein can be used in the practice of the present invention, the preferred systems and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

Finally, as used in this specification and the appended claims, the singular forms "a, "an" and "the" include plural referents unless the content clearly dictates otherwise. Thus, for example, reference to "a bioactive agent" includes two or more such agents.

Definitions

The term "compatibility", as used herein, includes, without limitation, an assessment of interactions between two or more bioactive agents or a bioactive agent and a pharmacological agent, including the degree of alteration by chemical interaction and alteration(s) of therapeutic effects. The term "compatibility" also includes an assessment of interactions between a bioactive agent and/or a pharmacological agent and a human or animal body.

The term "bioactive agent", as used herein, means and includes, without limitation, vitamins, minerals, hormones, enzymes, berry extracts, mushroom extracts, antioxidants, food extracts and pharmacological agents, e.g., medication(s).

The term "vitamin", as used herein, means and includes, without limitation, vitamins A, D, E, K, choline, the B Vitamin family, pantothenic acid, biotin and folate (folic acid).

The term "mineral", as used herein, means major minerals, including, without limitation, sodium, potassium, calcium, phosphorus, magnesium, sulfur, and chloride, and trace minerals, including, without limitation, iron, zinc, copper, selenium, iodine, chromium, manganese, fluoride, molybdenum, cobalt and others.

The terms "pharmacological agent", "pharmaceutical agent", and "medication" are used interchangeably herein, and mean and include an active agent, drug, compound, composition of matter or mixture thereof, including its formulation, which can provide some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

According to the invention, the pharmacological agents can comprise, for example, small molecules, such as steroids and NSAIDs, proteins, enzymes, hormones, oligonucleotides, polynucleotides, nucleoproteins, modified DNA and RNA loaded viruses with modified capsid, polysaccharides, glycoproteins, lipoproteins, polypeptides, including drug carriers, such as polymers, micro and nano particles.

Further examples of pharmacological agents include, without limitation, atropine, tropicamide, dexamethasone, dexamethasone phosphate, betamethasone, betamethasone phosphate, prednisolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, lidocaine, neomycin, polymyxin b, bacitracin, gramicidin, gentamicin, oyxtetracycline, ciprofloxacin, ofloxacin, tobramycin, amikacin, vancomycin, cefazolin, ticarcillin, chloramphenicol, miconazole, itraconazole, trifluridine, vidarabine, ganciclovir, acyclovir, cidofovir, ara-amp, foscarnet, idoxuridine, adefovir dipivoxil, methotrexate, carboplatin, phenylephrine, epinephrine, dipivefrin, timolol, 6-hydroxydopamine, betaxolol, pilocarpine, carbachol, physostigmine, demecarium, dorzolamide, brinzolamide, latanoprost, sodium hyaluronate, insulin, verteporfin, pegaptanib, ranibizumab, and other antibodies, antineoplastics, Anti VGEFs, ciliary neurotrophic factor, brain-derived neurotrophic factor, bFGF, Caspase-1 inhibitors, Caspase-3 inhibitors, α-Adrenoceptors agonists, NMDA antagonists, Glial cell line-derived neurotrophic factors (GDNF), pigment epithelium-derived factor (PEDF), NT-3, NT-4, NGF, IGF-2, antibiotics or antifungal drugs, anti-pain medication, anesthetics, and combinations thereof.

The term "excipient", as used herein, means and includes substantially inert materials that are nontoxic and do not interact with other components of a composition in a deleterious manner, including, without limitation, pharmaceutical grades of carbohydrates, including monosaccharides, disaccharides, cyclodextrins, and polysaccharides dextrose, sucrose, lactose, raffinose, mannitos, sorbitol, inositol, dextrins and maltodextrins); starch; cellulose; salts (e.g., sodium or calcium phosphates, calcium sulfate, magnesium sulfate); citric acid; tartaric acid; glycine; high molecular weight polyethylene glycols (PEG); polylactic acid (PLA); polylacticcoglygolic acid (PLGA); pluronics; surfactants; and combinations thereof. The term "excipient", as used herein, also includes biocompatible carriers, including, without limitation, human albumin, bioengineered human albumin, polyglutamic acid, polyaspartic acid, polyhistidine, pentosan polysulfate, polyamino acids, trehalose, melezitose, and stachyose, and stabilizing agents, including, without limitation, reducing sugars.

Suitable reducing sugars for use in the methods and compositions of the invention include, without limitation, monosaccharides such as, for example, apiose, arabinose, lyxose, ribose, xylose, digitoxose, fucose, quercitol, quinovose, rhamnose, allose, altrose, fructose, galactose, glucose, gulose, hamamelose, idose, mannose, tagatose, and the like; and disaccharides such as, for example, primeverose, vicianose, rutinose, scillabiose, cellobiose, gentiobiose, lactose, lactulose, maltose, melibiose, sophorose, and turanose, and the like.

As indicated above, the present invention includes methods and systems for determining compatibility by and between bioactive agents, as defined herein, by and between bioactive agents and the body, and, in some envisioned embodiments, by and between bioactive agents and food sources.

The method for determining compatibility of bioactive agents (i.e. supplement formulation components, pharmacological agents, etc.), in accordance with one embodiment of the invention, comprises the steps of determining compatibility by and between components contained in a supplement formulation, i.e. vitamins and/or minerals, determining compatibility by and between the formulation components and the body, and determining compatibility by and between the formulation components and pharmacological agents, i.e. prescribed and over-the-counter medications.

In some embodiments of the invention, the method also includes the step of determining compatibility by and between the formulation components and at least one food source.

According to the invention, the compatibility determination steps can be performed separately, i.e. solely determining compatibility by and between components contained in a supplement formulation, or collectively, as recited above. The determination steps can also be performed in any order.

In accordance with one embodiment of the invention, the system includes memory means adapted to store selective data and information, and programming means having a plurality of inter-related assessment modules, the assessment modules including a formulation compatibility module that is adapted to determine compatibility by and between components contained in a supplement formulation, a physiological compatibility module that is adapted to determine compatibility by and between the formulation components and the body, and a medicinal compatibility module that is adapted to determine compatibility by and between the formulation components and pharmacological agents, i.e. prescribed and over-the-counter medications.

Figure 2:
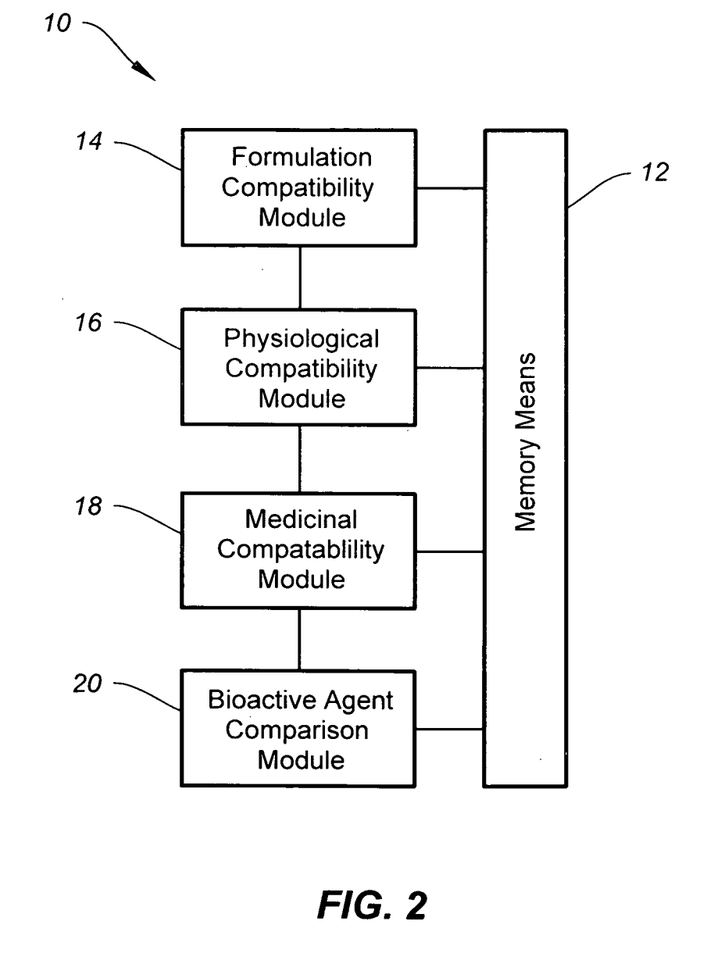
FIG. 2 is a schematic illustration of the inter-related compatibility modules, according to one embodiment of the invention.
Figure 4A:
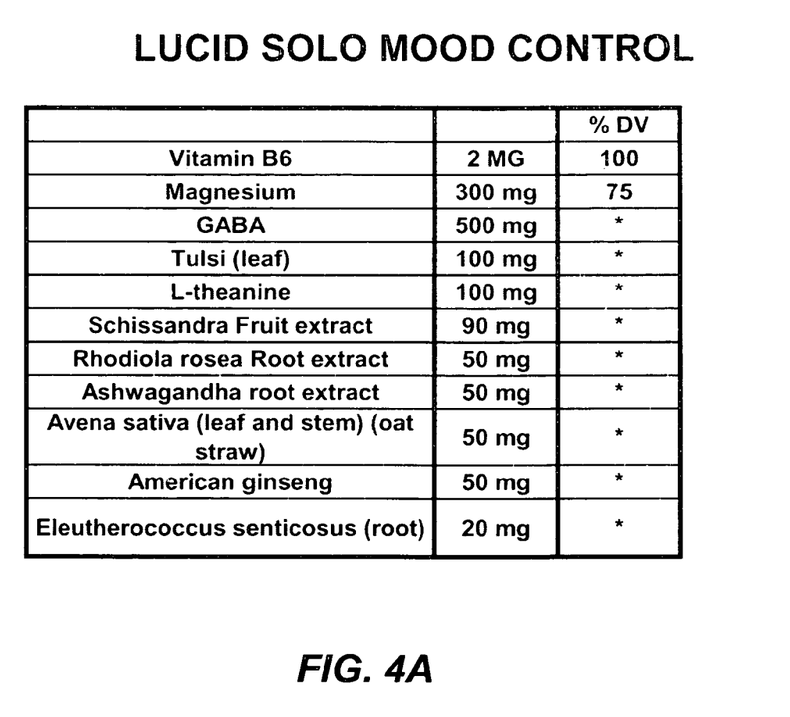
FIGS. 4A-4D are charts of several bioactive agent formulations, according to one embodiment of the invention.
Figure 4B:
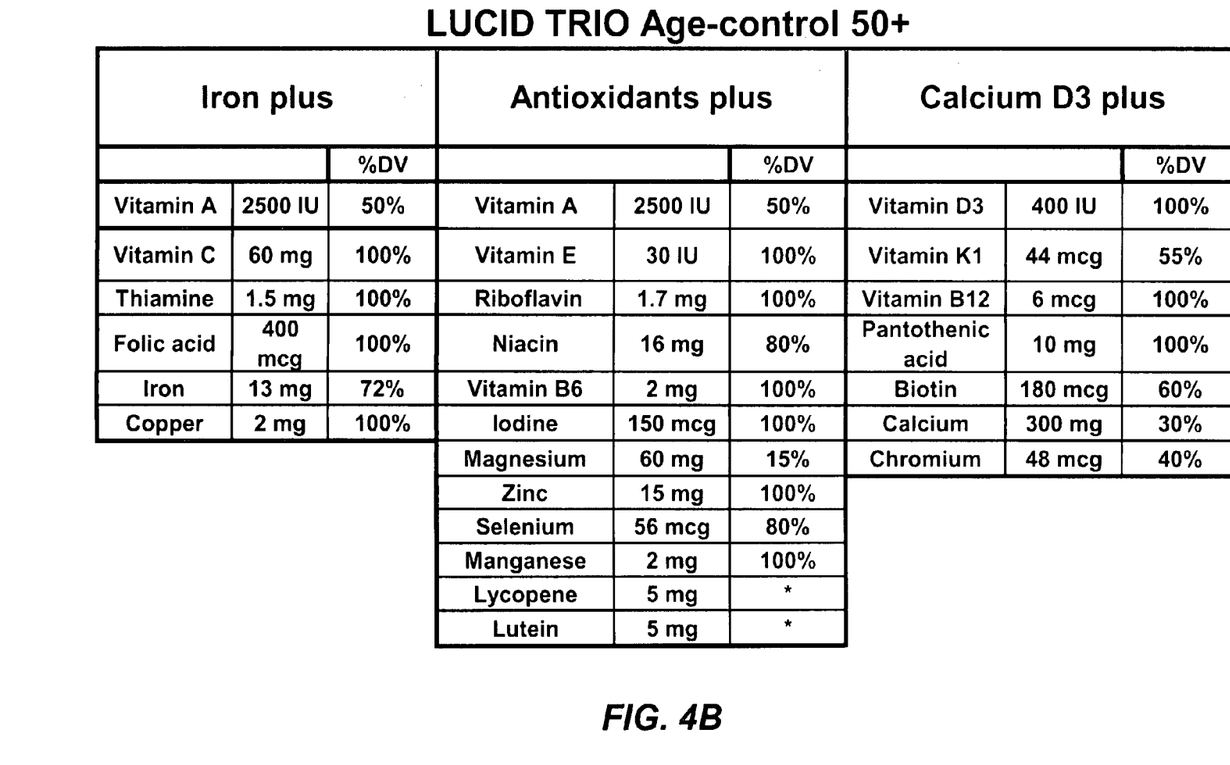
Figure 4C:
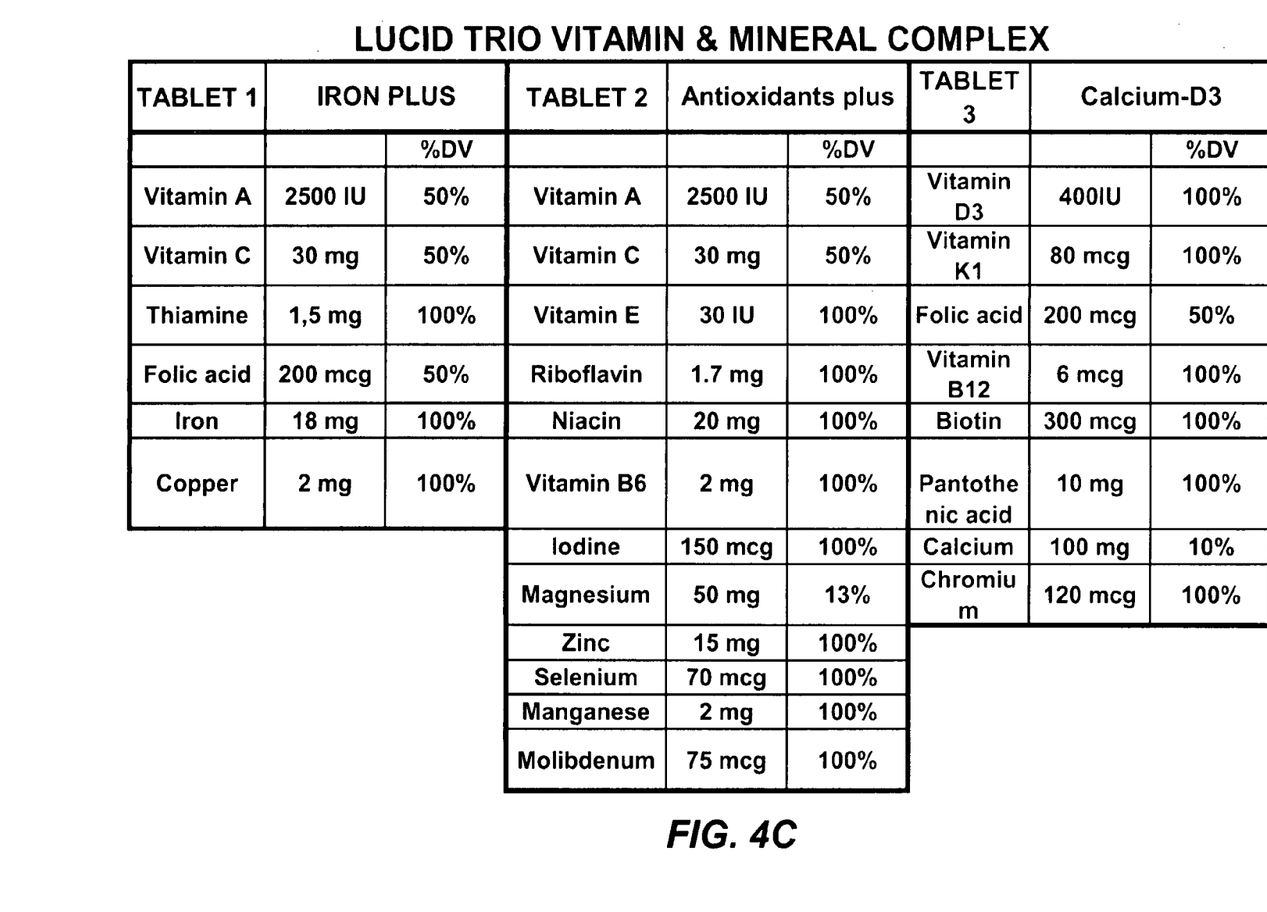
Figure 4D:
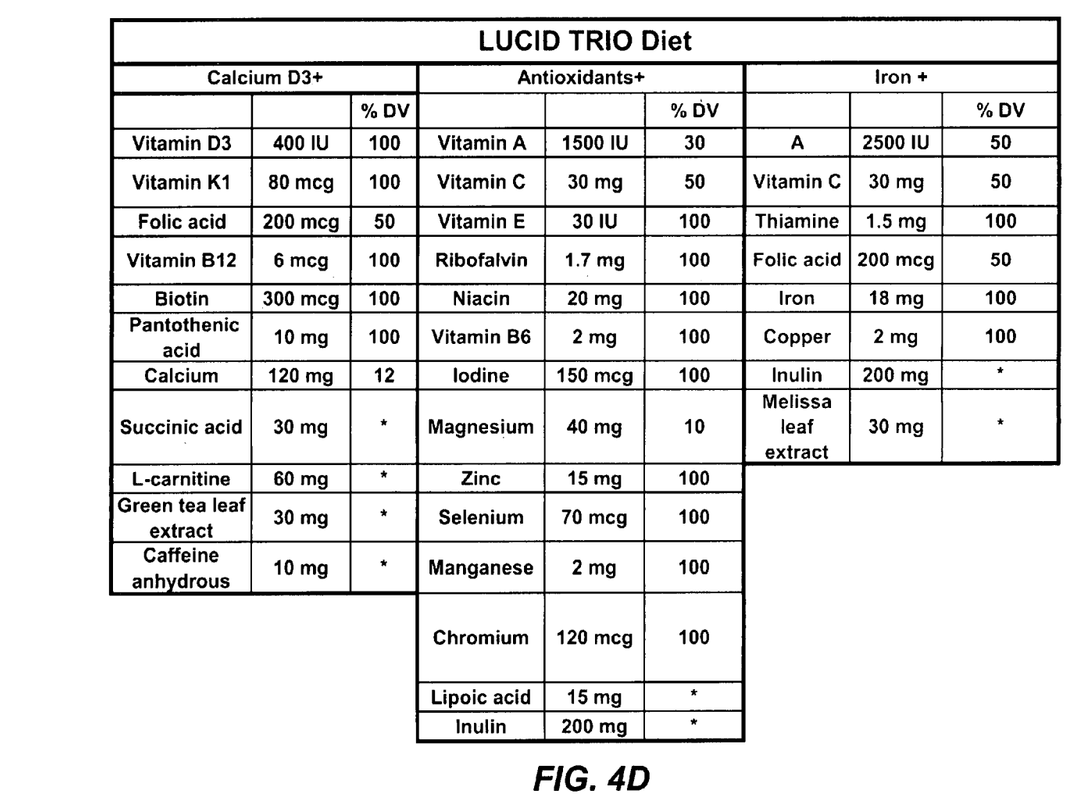

Referring to FIG. 2, there is shown a schematic illustration reflecting one embodiment of the bioactive agent compatibility system 10 of the invention. As illustrated in FIG. 2, the system 10 includes memory means 12, such as RAM and ROM, and the aforementioned formulation compatibility module 14, physiological compatibility module 16, and medicinal compatibility module 18.

In a preferred embodiment, the memory means 12 includes data and information relating to specific bioactive agents, including vitamins, minerals and pharmacological agents, and compatibility parameters associated therewith. The memory means 12 further includes data and information relating to bodily fluids and organs, and compatibility parameters associated therewith.

In an envisioned embodiment, the memory means 12 further includes data and information of selective foods.

In a preferred embodiment, the formulation compatibility module 14 includes at least one algorithm that is adapted to determine compatibility by and between components contained in a supplement (i.e. vitamin and/or mineral) formulation and/or at least one chart having compatibility indexes listed thereon. In at least one embodiment, the compatibility determination is based on the data and information stored in the memory means 12.

By way of example, in some embodiments of the invention, the compatibility indexes are based on the well known Gladstone-Dale Relationship, i.e.

$$(n-1)/d = \alpha \qquad \text{Eq. 1}$$

where:
n=mean index of refraction;
d=density; and
α=Gladstone-Dale constant.

In J. A. Mandarino, "The Gladstone-Dale Compatibility of Minerals and Its Use in Selecting Mineral Species for Further Study", *The Canadian Mineralogist*, vol. 19, pp 441-450 (1981), Mandarino employed the Gladstone-Dale relationship to compare the physical and optical properties of minerals and, thereby, derive a compatibility index for minerals. The compatibility index (CI) is defined as follows:

$$CI\ meas = (1 - KPD\text{meas}/KC) \qquad \text{Eq. 2}$$

$$CI\ calc = (1 - KPD\text{calc}/KC) \qquad \text{Eq. 3}$$

where:
KP=Gladstone-Dale Constant derived from physical properties; and
where:
KPDcalc=(n−1)/Dcalc; and
KPDmeas=(n−1)/Dmeas
and $$KC = \text{Sum of } (k1p1/100 + k2p2/100 \ldots + knpn/100) \quad \text{Eq. 4}$$

where:
The Gladstone-Dale constant is estimated from chemical analysis; and
where
kc=Gladstone-Dale constant of chemical phase "n"; and
kp=Percentage of the chemical phase "n".

The internal consistency of the compatibility index is defined in Table 11 below:

TABLE II

| Compatibility Index | Category |
|---|---|
| ±0.000 to ±0.019 | Superior |
| ±0.020 to ±0.039 | Excellent |
| ±0.040 to ±0.059 | Good |
| ±0.060 to ±0.079 | Fair |
| >±0.079 | Poor |

In a preferred embodiment, the physiological compatibility module 16 includes at least one algorithm that is adapted to determine compatibility by and between components contained in a supplement (i.e. vitamin and/or mineral) formulation and a person's body and/or at least one chart listing compatibility indexes for components contained in a supplement formulation and physiological factors associated with a person's body. In at least one embodiment, the compatibility determination is based on the data and information stored in the memory means 12.

In a preferred embodiment, the medicinal compatibility module 18 includes at least one algorithm that is adapted to determine compatibility by and between components contained in a supplement (i.e. vitamin and/or mineral) formulation and pharmacological agents, including prescribed and over-the-counter medications, and/or at least one chart containing compatibility indexes for components contained in a supplement formulation and pharmacological agents. In at least one embodiment, the compatibility determination is based on the data and information stored in the memory means 12.

According to the invention, the compatibility charts can be generated from data derived from various medical sources, such as the Mayo Clinic "Drugs and Supplements" listing, pharmaceutical disclosures, and research publications.

According to the invention, the data and information stored in the memory means 12 can be tailored to a specific person, whereby highly accurate compatibility assessments can be provided. In some embodiments, the information thus includes at least one, more preferably, a plurality of physiological factors, such as blood characteristics and sensitivities to specific bioactive agents, e.g. allergic reactions. In some embodiments, the information further includes hormone levels, and genome or genetic codes and parameters.

Referring back to FIG. 2, in some embodiments of the invention, the system 10 includes a bioactive agent comparison module 20 that is adapted to compare selected bioactive agents. According to the invention, the data and information contained in the bioactive agent comparison module can similarly be obtained from various medical sources, such as the Mayo Clinic pharmacological agent listings, pharma industry publications, pharmaceutical company disclosures, and research publications.

In envisioned embodiments, the system 10 further includes a food module that is adapted to determine and/or provide compatibility by and between components contained in a supplement (i.e. vitamin and/or mineral) formulation and/or pharmacological agents and food sources.

In some embodiments of the invention, the system 10 includes wireless communication means for receiving and transmitting data and information from/to a monitoring station, whereby a skilled person, e.g., physician, can assess the transmitted data.

In a preferred embodiment, the system 10 provides the following: (i) the actual or potential compatibility issue, (ii) an explanation of the mechanism of each interaction, (iii) the level of significance of the interaction (e.g. minor, moderate, major), and (iv) recommended course of action to manage the interaction.

In accordance with another embodiment of the invention, there are provided balanced bioactive formulations of vitamins and/or minerals tailored to an individual's specific physiology; the formulations being based on compatibility by and between supplement formulation components, such as shown in FIG. 3, formulation components and the body, and formulation components and pharmacological agents.

According to the invention, the formulations can be provided in various forms and shapes, and packaged by various conventional means, which can be dictated by, for example, age and food habits. As discussed in detail below, the formulations can also be color coded.

For example, in some embodiments of the invention, the formulations are contained in conventional blister packs, having three to five different color coded formulations or tablets (or any other formulation form) positioned in multiple rows. One color can also be used for one row of tablets.

Blisters containing one tablet of a single or multiple colors are also possible. Additionally, capsules, caplets, soft-gels and other known shapes or forms of nutritional delivery forms can have the same compatibility principles. Pill size for any delivery form type can also vary.

The blister or any other packaging form can also have different size pills in one form package. The pills might also contain special imprints lettering, numbers, logos, or blister or packaging itself might have imprint with lettering, numbering, etc.

As indicated above, the formulations can include various components. Thus, in some embodiments of the invention, one formulation can comprise a minimum amount of vitamin E and the mineral selenium; the other combination having at least vitamins K and D and calcium; the other formulation having at least vitamin K and calcium; one of the remaining formulations having a minimum amount of at least one mineral, e.g. iron and copper; another formulation having a minimum amount of another mineral, such as zinc and manganese.

According to the invention, in some embodiments of the invention, the packaged formulations can comprise as many as twenty (20) or more formulations of three (3) compositions, which are designed to be ingested within 24 hours and, in some embodiments, in 4-8 hour intervals.

Since it is well known in the art that (i) vitamin E and selenium, and vitamin K and calcium function synergistically, (ii) vitamin D is necessary for calcium absorption, and (iii) copper promotes absorption of iron, one or more of the formulations or combinations include synergistic amounts of the noted vitamins and minerals.

Since it is additionally known that excess of iron leads to deficiency of copper, and excess of manganese leads to deficiency of magnesium, the noted minerals are preferably provided in balanced, synergistic amounts.

Since it is also well known in the art that iron and calcium reduce absorption of manganese, and calcium reduces the absorption of iron, the noted components are preferably provided in separate combinations.

In some embodiments, the components, i.e. vitamins and minerals, are thus provided as follows: one formulation containing vitamins B1, B3, B6, and minerals iron, copper, molybdenum and iodine; and one formulation containing vitamins A, E, C, K, H, B2, B5, B6, B9, B12, D3, and minerals calcium, chromium, magnesium, manganese, selenium, and zinc.

In some embodiments of the invention, the formulations comprise more than three combinations or compositions. Thus, in one embodiment, the following four compositions are provided: (i) composition one comprising vitamins B1, B3, B6, and minerals iron and molybdenum, (ii) composition two comprising copper and iodine, (iii) composition three comprising vitamins B2, B3, B6, B9, B12, D3, H, K, and minerals calcium and chromium, and (iv) composition four comprising vitamins A, E, C, and minerals magnesium, manganese, selenium and zinc.

In one embodiment of the invention, the following five compositions are provided: (i) composition one comprising vitamins B1, B3, B6, and minerals iron and molybdenum, (ii) composition two comprising copper and iodine, (iii) composition three comprising vitamins B2, B9, B12, D3, K, and minerals calcium, potassium, magnesium and zinc, (iv) composition four comprising vitamins B5, B6, H, and mineral chromium, and (v) composition five comprising vitamins A, E, C, and minerals manganese and selenium.

According to the invention, all formulations (or compositions) of the invention can also contain various stabilizing and/or binding agents, including one or more of the aforementioned excipients.

The formulations can additionally include one or more known weight loss and/or appetite suppressant components, such as phentermine.

Referring now to FIGS. 4A-4D, there are shown several balanced bioactive formulations of the invention. According to the invention, the FDA established DV (Daily Value) is used in conjunction with the above mentioned compatibility determinations to derive the formulations of the invention.

In a preferred embodiment of the invention, the formulations of the invention are uniquely color coded to, among other things, distinguish a particular formulation (or tablet) and control defined sequential ingesting intervals, e.g. 4-8 hours between each tablet during the day with or after the meal. According to the invention, the ingesting intervals are, in some instances, desired for proper absorption of the formulation.

In some embodiments, intervals of 4-8 hours in between each tablet during the day with or after the meal are desired. The time lapse is intended for proper absorption due to antagonistic nature of some elements in vitamin/mineral complexes.

As indicated above, the formulations of the invention can be provided in various forms and shapes, and packaged by various conventional means, such as blister packs. Each formulation (or composition) can also be colored differently, and packaged such that solid forms of formulation can form individual rows of a single color.

According to the invention, the same principle of compatibility can be used in nutrocosmetics, including, without limitation, in cosmetics, baby foods and formulas, fortified foods, etc.

As will readily be appreciated by one having ordinary skill in the art, the present invention provides numerous advantages. A significant advantage is the provision of a method (and associated system) for determining compatibility by and between supplement (i.e. vitamin and/or mineral) formulation components, supplement formulation components and the body, and supplement formulation components and pharmacological agents prior to administration, whereby the effects on the bioactivity of the individual formulation components and/or pharmacological agents can be readily ascertained and the probability of adverse reactions therefrom can be substantially reduced or eliminated.

Additional advantages include the following:
(i) The provision of balanced bioactive vitamin and mineral formulations that improve the health of the population by providing compatible compositions of vitamins and minerals based on their intricate chemical structure and behavior;
(ii) The provision of balanced bioactive vitamin and mineral formulations that substantially reduce the probability of excessive intake of vitamins and minerals, while meeting existing USA FDA government levels of daily norms;
(iii) The provision of methods for determining compatibility of vitamin and mineral formulations that improve the absorption of various vitamins and minerals or other elements that are part of vitamin-mineral complexes or supplements by creating proper conditions for their synergistic interaction;
(iv) The provision of methods for determining compatibility of vitamin and mineral formulations that increase storage life for products containing compatible ingredients; and
(v) The provision of methods for determining compatibility of vitamin and mineral formulations that reduce manufacturing time by eliminating the need for multiple stabilizing agents in coatings, which are traditionally used in non compatible vitamin/mineral complexes.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A method for determining compatibility of bioactive agents for ingestion by a subject, comprising the steps of:
(i) determining compatibility by and between components contained in a supplement formulation and generating a first compatibility factor based thereon;
(ii) determining compatibility by and between said formulation components and a human body and generating a second compatibility factor based thereon;
(iii) determining compatibility by and between said formulation components and a pharmacological agent and generating a third compatibility factor based thereon; and
(iv) generating a bioactive agent profile based on said first, second and third compatibility factors that provides to the subject a compatible formulation of the bioactive agents;

including at least one algorithm for determining said compatibility by and between said components contained in said supplement formulation;

wherein the step of determining compatibility by and between said components contained in said supplement formulation includes the step of determining the components contained in at least two supplement formulations;

wherein a first of said at least two supplement formulations does not include a combination of bioactive agents that hinder absorption of any of the bioactive agents present in said first supplement formulation, and wherein a second of said at least two supplement formulations does not include a combination of bioactive agents that hinder absorption of any of the bioactive agents present in said second supplement formulation;

wherein said first supplement formulation is ingested by the subject during a first time period every 24 hours and wherein said second supplement formulation is ingested by the subject during a second time period every 24 hours, and wherein said second time period begins at least four hours after said first time period ends; and wherein ingesting of said first supplement formulation during said first time period and ingesting of said second supplement formulation during said second time period prevents any adverse interactions from occurring between any of the bioactive agents in said first supplement formulation and any of the bioactive agents in said second supplement formulation.

2. The method of claim 1, wherein said method includes the step of determining compatibility by and between said formulation components and at least one food source and generating a fourth compatibility factor based thereon and wherein said bioactive agent profile is generated based on said first, second, third and fourth compatibility factors.

3. The method of claim 1, wherein said first supplement formulation includes vitamins B1, B3, B6 and the minerals iron, copper molybdenum and iodine, and wherein said second formulation includes the vitamins A, E, C, K, H, B2, B5, B6, B9, B12, D3, and minerals calcium, chromium, magnesium, manganese, selenium, and zinc.

4. The method of claim 1, wherein said at least one algorithm includes determining compatibility of the bioactive agents based on the Gladstone-Dale Relationship.

5. A system for determining compatibility of bioactive agents, comprising:

memory means for storing compatibility data and information; and programming means for determining at least one compatibility factor, said programming means including a plurality of integral assessment modules, said assessment modules including a formulation compatibility module for determining compatibility by and between components contained in a supplement formulation and generating a first compatibility factor based thereon, a physiological compatibility module for determining compatibility by and between said formulation components and a human body and generating a second compatibility factor based thereon, and a medicinal compatibility module for determining compatibility by and between said formulation components and at least one pharmacological agent and generating a third compatibility factor based thereon, said programming means being further programmed to generate a bioactive agent profile based on said first, second, and third compatibility factors; wherein said formulation compatibility module includes at least one algorithm for determining said compatibility by and between said components contained in said supplement formulation, and wherein said at least one algorithm includes determining compatibility of the bioactive agents based on the Gladstone-Dale Relationship.

6. The system of claim 5, wherein said formulation compatibility module includes at least a first compatibility chart having supplement component compatibility indexes listed thereon for determining said compatibility by and between said components contained in said supplement formulation.

7. The system of claim 5, wherein said physiological compatibility module includes at least one algorithm for determining said compatibility by and between said supplement components and said body.

8. The system of claim 5, wherein said physiological compatibility module includes at least a second compatibility chart having physiological compatibility indexes listed thereon for determining said compatibility by and between said supplement components and said body.

9. The system of claim 8, wherein said body comprises a first subject and, wherein said physiological compatibility indexes are based on physiological characteristics associated with said first subject.

10. The system of claim 5, wherein said programming means generates a compatibility warning signal representing a first compatibility issue based on at least one of said first, second and third compatibility factors.

11. The system of claim 5, wherein said programming means generates a compatibility warning signal representing a second compatibility issue based on said bioactive agent profile.

* * * * *